United States Patent
Shah et al.

(12)

(10) Patent No.: US 6,303,105 B1
(45) Date of Patent: *Oct. 16, 2001

(54) COSMETIC COMPOSITION FOR IMPARTING WEAR RESISTANCE AND SHINE

(75) Inventors: Arvind N. Shah, Suffern, NY (US); Harold E. Pahlck, Waldwick, NJ (US); Ernest S. Curtis, Milford, PA (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,474

(22) Filed: Dec. 16, 1999

Related U.S. Application Data

(63) Continuation-in-part of application No. 09/162,052, filed on Sep. 28, 1998, now Pat. No. 6,083,516, which is a continuation of application No. 08/824,510, filed on Mar. 26, 1997, now abandoned.

(51) Int. Cl.$^7$ ........................................................ A61K 7/04
(52) U.S. Cl. ..................... 424/61; 424/70.1; 424/78.17; 424/401; 514/880
(58) Field of Search ............................ 424/61, 70.1, 407, 424/78.03, 78.17; 514/880

(56) References Cited

U.S. PATENT DOCUMENTS

| 4,792,444 | 12/1988 | Fukasawa et al. ...................... 424/63 |
| 5,030,374 | 7/1991 | Tranner .................................. 252/90 |
| 5,143,723 | 9/1992 | Calvo et al. ........................... 424/63 |
| 5,221,534 | 6/1993 | DesLauriers et al. ............. 424/78.03 |
| 5,676,935 | 10/1997 | Mellul et al. ........................... 424/61 |
| 5,807,540 | 9/1998 | Junino et al. .......................... 424/61 |

FOREIGN PATENT DOCUMENTS

WO 98/42298 * 10/1998 (WO).

* cited by examiner

Primary Examiner—Shelley A. Dodson
Assistant Examiner—Konata M. George
(74) Attorney, Agent, or Firm—Ohlandt, Greeley, Ruggiero & Perle, LLP

(57) ABSTRACT

There is provided a cosmetic composition having, as film formers, an alkyl cycloalkylacrylate copolymer having $C_{14}$ to $C_{36}$ repeating alkyl units, and an ester containing acids derived from rosin. The composition preferably includes a volatile solvent. The composition may include a block copolymer as a third film former. The composition is transfer and wear resistant and maintains a high shine.

26 Claims, No Drawings

COSMETIC COMPOSITION FOR IMPARTING WEAR RESISTANCE AND SHINE

This is a continuation-in-part of U.S. patent application Ser. No. 09/162,052 that was filed on Sep. 28, 1998 and issued as U.S. Pat. No. 6,083,516 on Jul. 4, 2000, which is a continuation of U.S. Pat. No. 08/824,510 that was filed on Mar. 26, 1997 and in now abandoned.

BACKGROUND OF THE INVENTION

1. Field of the Invention

The present invention relates to cosmetic compositions. More particularly, the present invention relates to cosmetic compositions applied to the lips, eyes, and face having improved wear resistance and long-lasting high shine.

2. Description of the Prior Art

Various organic waxes and film formers are known in the art for their ability to impart uniform films and protective barriers to the skin and lips. Most of these films have good shine but are slow to dry on application. Since these slow-drying films remain semi-wet for extended periods of time, products that have such film formers adhere poorly and tend to transfer off the surface to which they are applied. This results in poor overall cosmetic wear, and requires that the user reapply the cosmetic frequently.

Film formers that provide somewhat more rapid drying times, and hence better transfer resistance, have their own limitations. A primary limitation is an unpleasant tacky and "pulling" feel on application to the skin, lips, or lashes upon drying. Consumers dislike such a feel. Another limitation is the tendency of cosmetic products having such film formers to drag against the skin when applied, leaving the skin feeling dry and sticky.

In the past few years, various types of solvent-based transfer resistant cosmetic products have been available. Such products include lipsticks, eye shadows, blushes, foundations, mascaras, eyeliners, and lip liners. Transfer resistant solvent-based cosmetic products provide longer wear compared to conventional oil or wax-based systems. However, the applied product loses its shine once the solvent has evaporated. Longer lasting shine is preferred by cosmetic wearers.

U.S. Pat. No. 5,143,723 to Calvo, et al. provides for a colored cosmetic product having pigments formed by incorporating a solvated dye into a resin. Polymeric materials approved by the Food and Drug Administration as "indirect food additives" are especially preferred resins for use in this make-up composition. These resins include styrene block polymers and ethylene-methyl acrylate copolymer resins. However, this patent does not provide for cosmetics with transfer resistant characteristics.

U.S. Pat. No. 5,030,374 to Tranner, titled Clear Neutral Non-Foaming Rapidly-Rinseable Gel Facial Cleanser Formulation, has a block copolymer and an acrylic copolymer. Nonetheless, this patent also does not provide for cosmetics with transfer resistant characteristics.

U.S. Pat. No. 4,792,444 to Fukasawa, et al., titled Cosmetic Comprising Fluoroalkyl (Meth)Acrylate Copolymers, has a cosmetically acceptable volatile oil and at least one copolymer of a first monomer selected from fluoroalkyl acrylates or fluoroalkyl methacrylates, and a second monomer selected from alkyl acrylates or methacrylates. This patent does not provide a cosmetic product that maintains its shine once the volatile oil evaporates.

U.S. Pat. No. 5,807,540 to Junino, et al., titled Nail Varnish Composition Comprising a Crosslinked Polyester, has at least one film-forming material, a solvent medium, and at least one crosslinked polyester. The polyester is derived from the polycondensation of adipic acid, diethylene glycol, and a polyol having at least three hydroxyl groups. The film forming material may have a resin.

Thus, it is apparent that there remains a need to provide a cosmetic composition having transfer resistant characteristics while maintaining long-lasting high shine, flexibility, smoothness, and uniformity.

SUMMARY OF THE INVENTION

It is an object of the present invention to provide cosmetic compositions for application to the lips, eyes, and face that maintain a high shine after application.

It is another object of the present invention to provide such cosmetic compositions that have minimum transfer and improved wear characteristics.

It is still another object of the present invention to provide such cosmetic compositions having acceptable flexibility, smoothness, and uniformity.

These and other objects of the present invention are achieved by a cosmetic composition having, as film formers, (1) an alkyl cycloalkylacrylate copolymer having $C_{14}$ to $C_{36}$ repeating alkyl units, (2) an ester containing acids derived from rosin, and (3) a block copolymer. The composition preferably includes a volatile solvent. The composition is transfer/wear resistant and maintains a high shine.

DETAILED DESCRIPTION OF THE INVENTION

The present invention provides a wear-resistant cosmetic product or composition such as, a lipstick, foundation, eye shadow, lip liner, eyeliner, blush, or mascara. It has been unexpectedly discovered that the foregoing cosmetic compositions having a combination of the film formers and plasticizer described below have high shine (i.e. high releactive property) and transfer/wear resistance. Such a cosmetic composition is also flexible or non-brittle, smooth or non-tacky, and uniform when applied. A cosmetic composition having the film formers of the present invention is also easy to apply and has a pleasant feel when applied to the skin.

The first film former is one or more copolymers consisting of alkyl cycloalkylacrylate monomers. The preferred alkyl cycloalkylacrylate copolymers and the isomers thereof have the following formulas:

Formula A

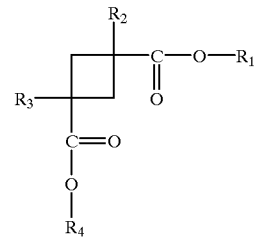

Formula B

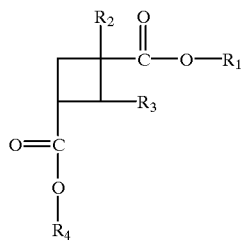

where $R_1$ to $R_4$ are each independently a hydrogen or a $C_{14}$ to $C_{36}$ alkyl group.

The preferred alkyl cycloalkylacrylate copolymers are soluble in hydrocarbons, such as isododecane, but not soluble in water. Thus, the film-forming effect of the copolymers is suitable for use in either an anhydrous system or a water-containing system.

Preferably, the alkyl cycloalkylacrylate copolymer for use in the present invention is a cycloalkyl methacrylate copolymer having $C_{14}$ to $C_{36}$ alkyl repeating units. A preferred cycloalkyl methacrylate copolymer is a bicycloalkyl methacrylate copolymer manufactured by Phoenix Chemicals, Inc., Somerville, N.J. and sold under the tradename Giovarez AC-5099 ML.

The one or more alkyl cycloalkylacrylate copolymers are preferably about 0.01 percent by weight (wt %) to about 75 wt % of the total composition. More preferably, the alkyl cycloalkylacrylate copolymers are about 10 wt % to about 25 wt %, and most preferably about 15 wt %.

The second film former is one or more esters containing acids derived from rosin. The preferred esters of the present invention are glyceryl rosinate, pentaerythrityl rosinate, silicone rosinate, and mixtures thereof. Esters of rosin acids are insoluble in water, thus enhancing the film-forming effect of the ester in a volatile solvent base.

The esters of rosin acids are preferably present in an amount about 0.10 wt % to about 20 wt %. More preferably, the esters of rosin acids are present in an amount about 2 wt % to about 15 wt %, and most preferably about 5 wt %.

The wear-resistant composition according to the present invention has at least one plasticizer, namely one or more block copolymers. Preferably, the block copolymers for use in the present invention are not water-soluble, but are soluble in certain oils and hydrocarbon solvents such as isoparaffin and isododecane. This solubility allows the block copolymers to be delivered to the skin by one or more volatile solvents. Once delivered, the volatile solvents evaporate, at least partially, leaving a water-insoluble, block copolymer film on the skin. This film resists transfer and wear.

Preferably, the block copolymers have styrene monomers, or other monomers derived from butylene, copolymerized with ethylene and propylene or butylene monomers. These block copolymers are known as styrene/ethylene/propylene tri-block copolymers and styrene/ethylene/butylene tri-block copolymers. Such tri-block copolymers act as plasticizers, as well as film formers. It should be understood that one or more mixed-block copolymers might be used in the present compositions. Furthermore, methods of preparing mixed-block copolymers are well known in the art.

A preferred styrene/ethylene/propylene (or butylene) tri-block copolymer consists of styrene, ethylene, and propylene (or butylene) monomers, or the derivatives thereof, having the general structures:

Structure A

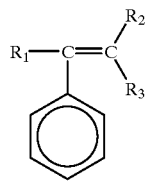

Structure B

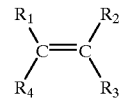

Structure C

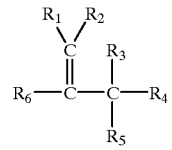

Structure D

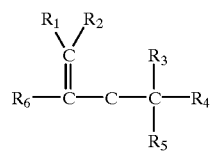

wherein $R_1$ to $R_6$ are each independently a hydrogen or a hydrophobic alkyl chain.

A preferred tri-block copolymer comprises styrene, propylene, and ethylene or butylene in a 4:2:1 ratio, with an average molecular weight of 10,000 to 20,000.

A preferred styrene/ethylene/propylene tri-block copolymer for use in the present invention is available from Brooks Industries, South Plainfield, N.J. under the tradename Gel Base I. Gel Base I comprises about 15 wt % of a styrene/ethylene/propylene tri-block copolymer dispersed in isododecane.

The one or more tri-block copolymers preferably are about 0.01 wt % to about 30 wt % of the total weight of the composition. Most preferably, the tri-block copolymers are about 0.10 wt % to about 10 wt %.

The present invention preferably includes one or more volatile solvents. A volatile solvent is generally understood as a solvent with a boiling point below about 100° C. at about 1.0 atmosphere. The one or more volatile solvents of the present invention act as carriers for the other ingredients of the composition and rapidly and evenly disperse these ingredients on the skin. Then, the one or more volatile solvents evaporate. The one or more volatile solvents may be an emulsion having anhydrous and hydrous components, or they may be substantially anhydrous. The hydrous solvent will generally be up to 30 wt % water, based on the total weight of the composition. The anhydrous volatile solvents will preferably include $C_6$ to $C_{20}$ hydrocarbon fractions, more preferably an isoparaffin and, most preferably, the specific $C_{12}$ fraction isododecane alone or in combination with the specific $C_1$ fraction isohexadecane.

The one or more volatile solvents may be about 0.01 wt % to about 80 wt % of the total weight of the composition. More preferably, the solvents are about 20 wt % to about 60 wt % and, most preferably, about 55 wt % of the total weight of the composition. However, in certain compositions, less than the maximum 80 wt % of the solvents is desired due to regulations on volatile organic chemicals.

It is also preferred, depending on the final product being formulated, that the composition include: a colorant such as an FD&C dye, titanium oxide, iron oxide, or zinc oxide; an emulsifier such as hydroxylated lanolin, or glyceryl pyroglutamate monooleate; a gelling agent such as fumed silica; a humectant such as propylene glycol; a chelating agent such an tetrasodium EDTA; a binder such as polybutene and lanolin alcohol; a preservative such as butylated hydroxytoluene, methylparaben, propylparaben, or phenoxyethanol; a plasticizer such as polyvinylpyrrolidone; a fragrance; an ultra-violet light screening agent; an electrolyte; a moisturizer; a vitamin; a mineral; an anti-oxidant; biotin; or combinations thereof. The composition may also include one or more filler ingredients, such as mica, talc, cosmetic wax, cosmetic powder, pearl, and glitter (a coated polyethylene base).

A preferred cosmetic composition according to the present invention has about 0.01 wt % to about 75 wt % of an alkyl cycloalkylacrylate copolymer; about 0.1 wt % to about 20 wt % of glyceryl rosinate, pentaerythritol rosinate, silicone rosinate, or mixtures thereof; and about 0.1 wt % to about 80 wt % volatile solvent. The cosmetic product also has about 0.01 wt % to about 10 wt % of a block copolymer of styrene monomers, or other derivatives of butylene, copolymerized with ethylene and propylene (or butylene) type monomers.

The composition of the present invention may further contain one or more ingredients selected from: a coloring agent, an emulsifier, a gelling agent, a plasticizer, a filler, a humectant, a preservative, a binding agent, a chelating agent, a fragrance, an ultraviolet light screening agent, an electrolyte, a moisturizer, a vitamin, a mineral, an antioxidant, biotin, and combinations thereof.

The following are examples of cosmetic compositions according to the present invention.

EXAMPLE 1

Liquid Gel for Lip, Eye, and Face

| Ingredient | wt % |
| --- | --- |
| Bicycloalkyl methacrylate copolymer | 0.1 to 75 |
| Glyceryl rosinate, pentaerythrityl rosinate, silicone rosinate, or combinations thereof | 0.1 to 20 |
| Styrene/ethylene/propylene tri-block copolymer | 0.1 to 30 |
| Volatile solvent such as isododecane | 0.1 to 80 |
| Plasticizer | 0.1 to 25 |
| Gelling agent | 0.1 to 10 |
| Coloring agent such as FD&C dyes, titanium dioxide, and zinc dioxide | 0.1 to 25 |
| Fillers such as treated or coated micas and talc, untreated or uncoated micas and talc, and glitter | 0.1 to 25 |

EXAMPLE 2

Waterproof Lash Paint

| Ingredient | wt % |
| --- | --- |
| Odorless mineral spirits | 32.00 |
| Demineralized water | 15.00 |
| Isodocecane | 15.00 |
| Cosmetic powder | 13.00 |
| Cosmetic wax | 9.00 |
| Iron oxide | 5.00 |
| Pentaerythritol rosinate | 2.50 |
| Block copolymer | 2.50 |

-continued

| Ingredient | wt % |
| --- | --- |
| Alkyl cycloalkylacrylate copolymer | 2.00 |
| Hydroxylated lanolin | 1.00 |
| Propylene glycol | 1.00 |
| Glyceryl pyroglutamate monooleate | 0.50 |
| 2-phenoxyethanol | 0.50 |
| Methylparaben | 0.50 |
| Tetrasodium EDTA | 0.20 |
| Acetylated POE lanolin alcohol | 0.20 |
| Polybutene | 0.10 |
|  | 100.00 |

The present invention having been described with particular reference to the preferred forms thereof, it will be obvious that various changes and modifications may be made herein without departing from the spirit and scope of the invention as defined in the appended claims.

Wherefore we claim:

1. A transfer resistant cosmetic composition comprising: an alkyl cycloalkylacrylate copolymer having $C_{14}$ to $C_{36}$ alkyl repeating units; an ester containing acids derived from rosin; and a plasticizer.

2. The cosmetic composition of claim 1, wherein said cycloalkyl methacrylate copolymer has a structure chosen from the group consisting of:

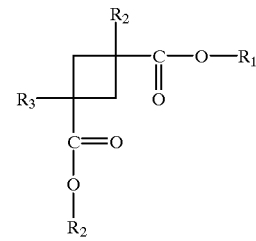

and

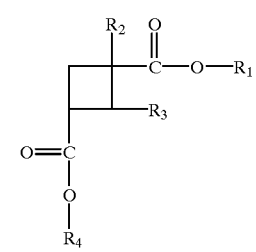

and mixtures thereof.

3. The composition of claim 1, wherein said ester of rosin acids is selected from the group consisting of glyceryl rosinate, pentaerythritol rosinate, silicone rosinate, and mixtures thereof.

4. The composition of claim 1, wherein said plasticizer is a block copolymer.

5. The composition of claim 4, wherein said block copolymer is about 0.01 wt % to about 30 wt %, based on the total weight of the composition.

6. The composition of claim 4, wherein said block copolymer is about 0.10 wt % to about 10 wt %, based on the total weight of the composition.

7. The composition of claim 4, wherein said block copolymer is a mixed-block copolymer comprised of monomers selected from the group consisting of propylene, ethylene, butylene, derivatives of butylene, and mixtures thereof.

8. The composition of claim 1, further comprising a volatile solvent.

9. The composition of claim 8, wherein said volatile solvent comprises anhydrous components derived from petroleum.

10. The composition of claim 8, wherein said volatile solvent comprises anhydrous components selected from the group consisting of isododecane, isohexadecane, and mixtures thereof.

11. The composition of claim 8, wherein said volatile solvent is about 0.01 wt % to about 80 wt %, based on the total weight of the composition.

12. The composition of claim 8, wherein said volatile solvent is about 20 wt % to about 60 wt %, based on the total weight of the composition.

13. The composition of claim 1, wherein said alkyl cycloalkylacrylate copolymer is about 0.01 wt % to about 75 wt %, based on the total weight of the composition.

14. The composition of claim 1, wherein said alkyl cycloalkylacrylate copolymer is about 10 wt % to about 25 wt %, based on the total weight of the composition.

15. The composition of claim 1, wherein said ester of rosin acids is about 0.10 wt % to about 20 wt %, based on the total weight of the composition.

16. The composition of claim 1, wherein said ester of rosin acids is about 2 wt % to about 15 wt %, based on the total weight of the composition.

17. A method of improving transfer resistance and/or shine of a cosmetic composition, comprising:

combining into said composition, based on the total weight of the composition:

about 0.01 wt % to about 75 wt % alkyl cycloalkylacrylate copolymer having $C_{14}$ to $C_{36}$ alkyl repeating units;

about 0.10 wt % to about 20 wt % of one or more esters containing acids derived from rosin; and about 0.01 wt % to about 30.0 wt % of plasticizer; and applying said composition onto a person.

18. The method of claim 17, wherein the composition further comprises about 0.10 wt % to about 80 wt % of a volatile solvent, based on the total weight of the composition.

19. The method of claim 17, wherein said plasticizer is a block copolymer.

20. The method of claim 19, wherein said copolymer is a mixed-block copolymer comprised of monomers selected from the group consisting of propylene, ethylene, butylene, derivatives thereof, and mixtures thereof.

21. The composition of claim 1, wherein said ester of rosin acids includes a silicone rosinate.

22. The method of claim 17, wherein said ester of rosin acids includes a silicone rosinate.

23. A method of enhancing/improving shine provided by a cosmetic composition, comprising:

adding an ester having acids derived from rosin to the composition.

24. The method of claim 23, wherein said ester is about 0.10 wt % to about 20 wt % based on the total weight of the composition.

25. The method of claim 23, wherein said ester is selected from the group consisting of glyceryl rosinate, pentaerythritol rosinate, silicone rosinate, and mixtures thereof.

26. The method of claim 23, wherein said ester includes a silicone rosinate.

* * * * *